US012607624B2

(12) United States Patent
Berg et al.

(10) Patent No.: US 12,607,624 B2
(45) Date of Patent: Apr. 21, 2026

(54) METHOD FOR ENHANCED DETERMINATION OF ANALYTE CONCENTRATION IN BODY FLUID

(71) Applicant: Roche Diabetes Care, Inc., Indianapolis, IN (US)

(72) Inventors: Max Berg, Mannheim (DE); Fredrik Hailer, Limburgerhof (DE); Bernd Limburg, Soergenloch (DE)

(73) Assignee: Roche Diabetes Care, Inc, Indianapolis, IN (US)

( * ) Notice: Subject to any disclaimer, the term of this patent is extended or adjusted under 35 U.S.C. 154(b) by 900 days.

(21) Appl. No.: 17/819,230

(22) Filed: Aug. 11, 2022

(65) Prior Publication Data

US 2022/0381773 A1 Dec. 1, 2022

Related U.S. Application Data

(63) Continuation of application No. PCT/EP2021/053119, filed on Feb. 10, 2021.

(30) Foreign Application Priority Data

Feb. 13, 2020 (EP) .................................... 20157055

(51) Int. Cl.
*G01N 33/52* (2006.01)
*B01L 3/00* (2006.01)
(Continued)

(52) U.S. Cl.
CPC ............ *G01N 33/52* (2013.01); *B01L 3/5023* (2013.01); *G01N 21/78* (2013.01);
(Continued)

(58) Field of Classification Search
CPC .................. G01N 33/52; G01N 21/78; G01N 2021/7759; G01N 2201/1211;
(Continued)

(56) References Cited

U.S. PATENT DOCUMENTS 7,947,222 B2   5/2011   Bae et al.
9,326,097 B2   4/2016   Sen et al.
(Continued)

FOREIGN PATENT DOCUMENTS

CN      107655889 A     2/2018
EP      3 018 470 A1    5/2016
(Continued)

OTHER PUBLICATIONS

International Search Report and Written Opinion of the International Searching Authority, PCT/EP2021/053119, Jun. 14, 2021, 11 pages.

(Continued)

*Primary Examiner* — Dennis White
(74) *Attorney, Agent, or Firm* — Bose McKinney & Evans LLP

(57) ABSTRACT

An analytical method for determining a concentration of an analyte is disclosed. In this method, an image of an optical test strip having a body fluid applied thereto is obtained with a camera of a mobile device. Local temperature information is received at a current location of the mobile device from a temperature source such as a remote weather information service or temperature sensor. Additional local temperature information is received by the mobile device from a thermochromic field provided on the test strip and/or on a color reference card. A processor determines a correction temperature and/or a correction temperature function using the local temperature information. The processor also determines the analyte concentration from the image captured and taking into account the correction temperature information.

15 Claims, 1 Drawing Sheet

(51) Int. Cl.
  *G01N 21/77* (2006.01)
  *G01N 21/78* (2006.01)

(52) U.S. Cl.
  CPC . *B01L 2300/022* (2013.01); *B01L 2300/0663* (2013.01); *B01L 2300/069* (2013.01); *B01L 2300/10* (2013.01); *G01N 2021/7759* (2013.01); *G01N 2201/1211* (2013.01)

(58) Field of Classification Search
  CPC ..... G01N 33/48792; G01N 2201/0221; G01N 2201/1273; B01L 3/5023; B01L 2300/022; B01L 2300/0663; B01L 2300/069; B01L 2300/10
  See application file for complete search history.

(56) References Cited

U.S. PATENT DOCUMENTS

| | | | |
|---|---|---|---|
| 9,778,200 | B2 | 10/2017 | Tsai et al. |
| 9,784,624 | B2 | 10/2017 | Niederberger et al. |
| 2008/0255434 | A1 | 10/2008 | Hayter et al. |
| 2010/0259394 | A1 | 10/2010 | Bae et al. |
| 2013/0267032 | A1 | 10/2013 | Tsai et al. |
| 2014/0170757 | A1 | 6/2014 | Tsai et al. |
| 2014/0284223 | A1 | 9/2014 | Malecha et al. |
| 2015/0316419 | A1 | 11/2015 | Punnakkal |
| 2016/0054021 | A1 | 2/2016 | Lee et al. |
| 2016/0125600 | A1* | 5/2016 | Lee .................... G01N 21/8483 382/128 |
| 2019/0223765 | A1 | 7/2019 | Harley-Trochimczyk et al. |

FOREIGN PATENT DOCUMENTS

| | | |
|---|---|---|
| EP | 3 575 781 A2 | 12/2019 |
| EP | 3 578 959 A2 | 12/2019 |
| JP | 2015-536465 A | 12/2015 |
| JP | 2016-503880 A | 2/2016 |
| KR | 10-2016-0052442 A | 5/2016 |
| RU | 2 626 048 C2 | 7/2017 |
| TW | 201721129 A | 6/2017 |
| WO | WO 2013/116831 A1 | 8/2013 |
| WO | WO 2013/119266 A1 | 8/2013 |
| WO | WO 2013/149598 A1 | 10/2013 |
| WO | WO 2014/094442 A1 | 6/2014 |
| WO | WO 2017/056002 A1 | 4/2017 |
| WO | WO 2019/082467 A1 | 5/2019 |

OTHER PUBLICATIONS

Hönes et al., The Technology Behind Glucose Meters: Test Strips, Diabetes Technology & Therapeutics, vol. 10, Supplement 1, 2008, pp. S-10-S-26.

* cited by examiner

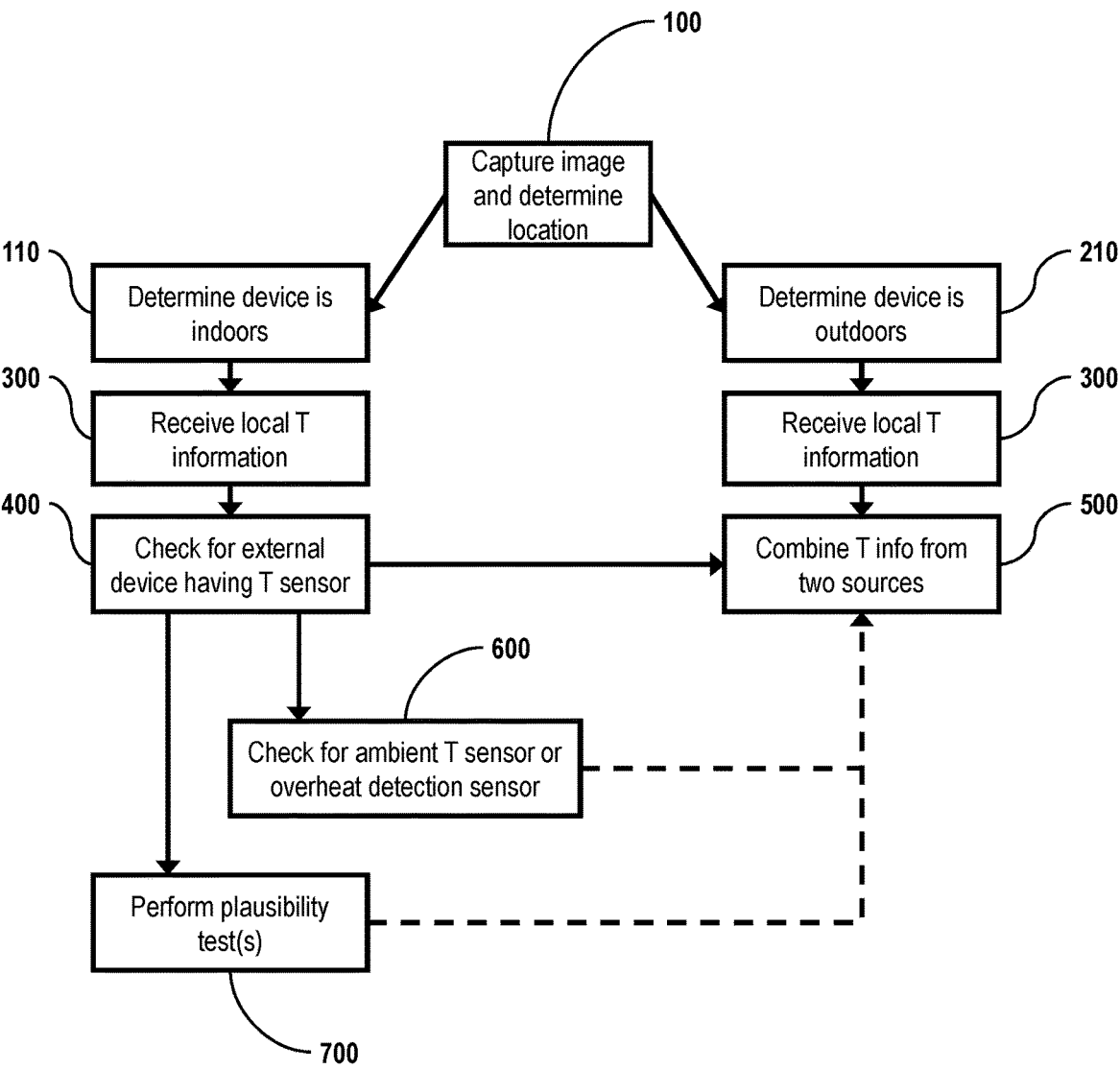

METHOD FOR ENHANCED DETERMINATION OF ANALYTE CONCENTRATION IN BODY FLUID

RELATED APPLICATIONS

This application is a continuation of PCT/EP2021/053119, filed Feb. 10, 2021, which claims priority to EP 20 157 055.3, filed Feb. 13, 2020, both of which are hereby incorporated herein by reference.

BACKGROUND

This disclosure relates to a method of determining a concentration of an analyte in a body fluid, using at least one mobile device having a camera and a processor. Further, this disclosure relates to a mobile device having a camera and a processor for carrying out the method, to a kit comprising a mobile device having a camera and a processor, to computer programs and computer-readable storage media. The methods, mobile devices, computer programs and storage media specifically may be used in medical diagnostics, for example, in order to qualitatively or quantitatively detect one or more analytes in body fluids, such as for detecting glucose in blood or interstitial fluid.

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of test elements comprising one or more test chemicals, which, in the presence of the analyte to be detected, are capable of performing one or more detectable detection reactions, such as optically detectable detection reactions. With regard to the test chemicals comprised in test elements, reference may be made, e.g., to J. Hoenes et al.: The Technology Behind Glucose Meters: Test Strips, Diabetes Technology & Therapeutics, Volume 10, Supplement 1, 2008, S-10 to S-26.

In analytical measurements, specifically analytical measurements based on color formation reactions, one technical challenge resides in the evaluation of the color change which is due to the detection reaction. Besides using dedicated analytical devices, such as handheld blood glucose meters, the use of generally available electronics such as smart phones and portable computers or other mobile devices has become more and more popular over recent years.

As opposed to laboratory measurements and measurements performed by using dedicated analytical measurement devices, when using mobile computing devices such as smart phones, various additional influencing factors need to be taken into account, such as, for example, lighting conditions and positioning aspects, which may be rather difficult to take into account. In order to improve the accuracy of results of analyte detection in these cases nonetheless, it is therefore beneficial to appropriately take into account any parameters known to be involved in the desired analyte detection or measurement.

For analytical measurements based on test chemicals, one such parameter usually is the temperature at which a reaction of an analyte with test chemicals takes place, see with regard to such test chemicals comprised in test elements, e.g., the above-cited reference to J. Hoenes et al.

When using mobile devices, one approach to take the temperature of a reaction on a test element into account is to provide a temperature sensor or a temperature indication area right on the test strip itself.

For example, U.S. Pat. No. 9,778,200 B2 describes a method for a portable computing device having an image sensor and a screen on a same side of the portable computing device to read a reaction area on a test strip, which is located in a peripheral device, the method comprising inter alia: providing light to illuminate the reaction area; capturing an image with the image sensor substantially free from ambient light; and determining an analyte characteristic based on a color of the captured reaction area in the image. The test strip may include a temperature sensor which can be read electrically to determine a temperature of the test strip, and an analyte characteristic may be corrected based on the temperature of the test strip; or the test strip may include a temperature indication area, and a specimen characteristic may be corrected based on the captured temperature indication area in the image.

EP 3 018 470 A1 describes a method of a terminal measuring biometric information, the method comprising: receiving an image of a biosensor comprising a reagent pad on which a sample is collected; and comparing brightness information of a reacting region of the reagent pad in the received image with reference brightness information in the received image to determine a value of a reagent reaction between the reagent pad and the sample. The method may further comprise determining a temperature of the sample based on temperature information that is indicated by a temperature measurer that is attached to the reagent pad in the received image.

When determining ambient temperatures with a mobile device, care needs to be taken to compensate for any impacts on temperature measurement from the mobile device itself, such as heat generated by any components of the mobile device.

An approach to address this aspect is described, e.g., in U.S. Pat. No. 9,784,624 B2 directed to a portable electronic device, comprising a temperature sensor for sensing an ambient temperature and at least one other temperature sensor for sensing a temperature inside the portable electronic device, a set of components radiating heat in an active state, a calibration module, and a compensator for determining a compensated ambient temperature dependent on at least the sensed ambient temperature and at least one adjusted sensed inside temperature, wherein the calibration module is adapted to conduct a calibration measurement in response to a powering on of the portable electronic device subsequent to a powered-down or a stand-by state.

Another approach to address this aspect is described in U.S. Pat. No. 7,947,222 B2 directed to a mobile communication terminal equipped with temperature compensation function for use in bio-information measurement, including a biosensor insertion into which a biosensor directly detecting bio-information of a subject is inserted, a temperature measurement unit, and a controller analyzing the bio-information, wherein the temperature measurement unit measures temperatures of a biosensor housing without contacting the biosensor housing directly and with the biosensor completely outside the biosensor housing, and wherein the controller corrects the bio-information using the temperature of the biosensor housing measured by the temperature measurement unit.

Furthermore, U.S. Pat. No. 9,326,097 B2 describes an approach to sense a surrounding of a mobile device by using information from sensors of a mobile device, which may include a temperature sensor, in combination with receiving a weather condition from a remote server in order to determine whether the mobile device is likely to be indoor or outdoor based on one or more weighted outputs from the sensors, wherein a timing for determining whether the mobile device is indoor or outdoor is adjusted, wherein a GPS receiver is used to determine how many satellites' signals can be received, and wherein it is determined that the mobile device is likely to be indoor if a number of satellites with receivable signals is below a threshold.

U.S. Publication No. 2013/0267032 A1 and EP 3 575 781 A2 relate to a specimen test strip to detect a characteristic of an analyte in a specimen sample, comprising a reaction area configured to receive the specimen sample; and a color calibration area configured to determine a color of the reaction area after receiving the specimen sample, wherein the specimen test strip may further comprise a temperature indication area configured to correct a measurement of the characteristic of analyte; and wherein a computing device may use a built-in temperature sensor to approximate or determine the temperature of a reaction area.

Despite the advantages involved in using mobile computing devices for the purpose of performing an analytical measurement, one of the remaining technical challenges still is to appropriately take into account a temperature of a reaction involving an analyte to be detected and test chemicals comprised in test elements.

SUMMARY

This disclosure at least partially addresses the above-mentioned challenge. Specifically, devices and methods are taught herein which allow for an efficient mobile-based determination of a concentration of an analyte in a body fluid with reliable accuracy and with low effort for setup and implementation.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "image," "sample," and "test region," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a method for determining a concentration of an analyte in a body fluid is disclosed, the method comprising using a mobile device having a camera and a processor. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed. The method comprises, in a first step i), capturing at least one image of at least a part of an optical test strip having a sample of the body fluid applied onto a reagent test region of the test strip, wherein the capturing comprises using the camera of the mobile device. The at least one image captured comprises at least a part of the reagent test region having the sample of the body fluid applied thereto. The method further comprises determining, by the processor, the analyte concentration from the image captured, based on a color formation reaction at the reagent test region having the sample of the body fluid applied thereto.

The method further comprises:

ii) receiving local temperature information at a current location of the mobile device, wherein said local temperature information is received by the mobile device from at least two of the following temperature source options:

a) a remote weather information service;

b) a temperature sensor of an external electronic device; and c) a temperature sensor of the mobile device;

or wherein said local temperature information is received by the mobile device from a temperature sensor of an external electronic device.

In step ii), the external electronic device is selected from one or more of wearables, such as fitness trackers, smart watches, smart glasses, smart clothing; smart-home components, such as electronic heating systems, smart temperature measurement units, home weather stations; and body-worn sensors, such as non-invasive analyte measurement sensors. Some more details of such external electronic devices are described herein below.

Optionally, the method may further comprise:

iii) determining, by the processor, a correction temperature and/or a correction temperature function, using the local temperature information from step ii).

The determining, by the processor, of the analyte concentration from the image captured, based on a color formation reaction at the reagent test region having the sample of the body fluid applied thereto, takes into account at least one of the local temperature information from step ii), the correction temperature from step iii), and the correction temperature function from step iii).

Without narrowing the scope, this disclosure specifically may be described with respect to blood glucose measurements. It shall be noted, however, that this disclosure may also be used for other types of analytical measurements using test elements.

The term "determining a concentration of an analyte in a body fluid," also referred to as an "analytical measurement," as used herein, is a broad term and is to be given its ordinary and customary meaning to a person of ordinary skill in the art and is not to be limited to a special or customized meaning. The term specifically may refer, without limitation, to a quantitatively and/or qualitatively determination of at least one analyte in an arbitrary sample or aliquot of body fluid. For example, the body fluid may comprise one or more of blood, interstitial fluid, urine, saliva or other types of body fluids, particularly blood. The result of the determining of the concentration, as an example, may be a concentration of the analyte and/or the presence or absence of the analyte to be determined. Specifically, as an example, the analytical measurement may be a blood glucose measurement, thus the result of the analytical measurement may, for example, be a blood glucose concentration. In particular, an analytical measurement result value may be determined by the analytical measurement.

Consequently, the term "analyte concentration value," often also referred to as "analytical measurement result value," as used herein, is a broad term and is to be given its ordinary and customary meaning to a person of ordinary skill in the art and is not to be limited to a special or customized meaning. The term specifically may refer, without limitation, to a numerical indication of an analyte concentration in a sample.

The at least one analyte, as an example, may be or may comprise one or more specific chemical compounds and/or other parameters. As an example, one or more analytes may be determined which take part in metabolism, such as blood glucose. Additionally or alternatively, other types of analytes or parameters may be determined, e.g., a pH value.

The method, as outlined above, comprises using at least one mobile device having at least one camera. The term "mobile device" as used herein is a broad term and is to be given its ordinary and customary meaning to a person of ordinary skill in the art and is not to be limited to a special or customized meaning. The term specifically may refer, without limitation, to a mobile electronics device, more specifically to a mobile communication device such as a cell phone or smartphone. Additionally or alternatively, the mobile device may also refer to a tablet computer or another type of portable computer having at least one camera and at least one processor.

The term "camera" as used herein is a broad term and is to be given its ordinary and customary meaning to a person of ordinary skill in the art and is not to be limited to a special or customized meaning. The term specifically may refer, without limitation, to a device having at least one imaging element configured for recording or capturing spatially resolved one-dimensional, two-dimensional or even three-dimensional optical data or information. As an example, the camera may comprise at least one camera chip, such as at least one CCD chip and/or at least one CMOS chip configured for recording images. As used herein, without limitation, the term "image" specifically may relate to data recorded by using a camera, such as a plurality of electronic readings from the imaging device, such as the pixels of the camera chip.

The camera, besides the at least one camera chip or imaging chip, may comprise further elements, such as one or more optical elements, e.g., one or more lenses. As an example, the camera may be a fix-focus camera, having at least one lens which is fixedly adjusted with respect to the camera. Alternatively, however, the camera may also comprise one or more variable lenses which may be adjusted, automatically or manually. This disclosure specifically shall be applicable to cameras as usually used in mobile applications such as notebook computers, tablets or, specifically, cell phones such as smart phones. Thus, specifically, the camera may be part of a mobile device which, besides the at least one camera, comprises one or more data processing devices such as one or more data processors. Other cameras, however, are feasible.

The method further comprises using at least one optical test strip having at least one reagent test region, also referred to as a "test field" herein. The term "optical test strip" as used herein is a broad term and is to be given its ordinary and customary meaning to a person of ordinary skill in the art and is not to be limited to a special or customized meaning. The term specifically may refer, without limitation, to an arbitrary element or device configured for performing a color-change detection reaction. The optical test strip may also be referred to as test strip or test element, wherein all three terms may refer to the same element. The optical test strip may particularly have a reagent test region containing at least one test chemical for detecting at least one analyte. The optical test strip, as an example, may comprise at least one substrate, such as at least one carrier, with the at least one reagent test region applied thereto or integrated therein. In particular, the optical test strip may further comprise one or more reference areas, such as a white field and/or a black field. Additionally or alternatively, the substrate or carrier itself may be or may comprise such a reference area. As an example, the at least one carrier may be strip-shaped, thereby rendering the test element a test strip. These test strips are generally widely in use and available. One test strip may carry a single test field or a plurality of test fields having identical or different test chemicals comprised therein.

As further used herein, the term "reagent test region" (also referred to as a "test field" herein) is a broad term and is to be given its ordinary and customary meaning to a person of ordinary skill in the art and is not to be limited to a special or customized meaning. The term specifically may refer, without limitation, to a coherent amount of the test chemical, such as to a field, e.g., a field of round, polygonal or rectangular shape, having one or more layers of material, with at least one layer of the test field having the test chemical comprised therein. With regard to the test chemicals comprised in optical test strips, as an example reference is made to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing this disclosure.

As outlined above, the method comprises capturing at least one image of at least a part of the reagent test region having the sample of the body fluid applied thereto, by using the camera. The term "capturing at least one image" as used herein is a broad term and is to be given its ordinary and customary meaning to a person of ordinary skill in the art and is not to be limited to a special or customized meaning. The term specifically may refer, without limitation, to one or more of imaging, image recording, image acquisition, image capturing. The term "capturing at least one image" may comprise capturing a single image and/or a plurality of images such as a sequence of images. For example, the capturing of the image may comprise recording continuously a sequence of images such as a video or a movie. The capturing of the at least one image may be initiated by the user action or may automatically be initiated, e.g., once the presence of the at least one object within a field of view and/or within a predetermined sector of the field of view of the camera is automatically detected. These automatic image acquisition techniques are known, e.g., in the field of automatic barcode readers, such as from automatic barcode reading apps. The capturing of the images may take place, as an example, by acquiring a stream or "life stream" of images with the camera, wherein one or more of the images, automatically or by user interaction such as pushing a button, are stored and used as the at least one first image or the at least one second image, respectively. The image acquisition may be supported by a processor of the mobile device, and the storing of the images may take place in a data storage device of the mobile device.

The capturing of the at least one image may comprise capturing at least one image with having the sample of the body fluid applied to the test strip and, further and optionally, such as before capturing the image with the sample applied to the test strip, capturing at least one image without having the sample of the body fluid applied to the test strip. The latter image specifically may be used for comparative purposes and may also be referred to as a "blank image" or "dry image". The sample application generally may take place, as an example, directly or indirectly, e.g., via at least one capillary element. The at least one image captured after sample application may typically also be referred to as the "wet image," even though the sample may have dried when the image is actually captured. The wet image typically may be taken after having waited for at least a predetermined waiting time, such as after five seconds or more, in order to allow for the detection reaction to take place. Thus, as an example, the method may comprise, between taking the at least one optional dry image and the at least one wet image, waiting for at least a predetermined minimum amount of time. This predetermined minimum amount of time specifically may be sufficient for a detection reaction to take place in the test strip. As an example, the minimum amount of waiting time may be at least 5 s.

The method comprises determining the analyte concentration, particularly an analyte concentration value, from color formation of the test field. Thus, the method may be an analytical measurement including a change of at least one optical property of an optical test strip, which change may be measured or determined visually by using the camera. Specifically, the analytical measurement may be or may comprise a color formation reaction in the presence of the at least one analyte to be determined. The term "color formation reaction" as used herein is a broad term and is to be given its ordinary and customary meaning to a person of ordinary skill in the art and is not to be limited to a special or customized meaning. The term specifically may refer, without limitation, to a chemical, biological or physical reaction during which a color, specifically a reflectance, of at least one element involved in the reaction, changes with the progress of the reaction. The color formation may be detected by the mobile device, such as by a processor of the mobile device, and may be evaluated quantitatively, such as by deriving, from the at least one image, at least one parameter quantifying or characterizing the color formation of the test field due to the presence of the analyte in the body fluid. To this end, one or more specific color coordinates may be used. Thus, the mobile device and specifically the processor of the mobile device may be configured for determining a color change by determining a change of one or more color coordinates taking place due to the detection reaction.

The at least one analyte concentration, particularly analyte concentration value, is determined from the color formation of the test field. For this purpose, the at least one image is used. The analyte concentration value, as an example, may be a numerical value indicator of a result of the analytical measurement, such as indicative of the concentration of at least one analyte in the sample, such as a blood glucose concentration.

The term "local temperature information" as used herein is a broad term and is to be given its ordinary and customary meaning to a person of ordinary skill in the art and is not to be limited to a special or customized meaning. The term specifically may refer, without limitation, to any information on a temperature which is measured or which can be assumed at a current location of the mobile device. The information on local temperature may be represented as a numerical value in any well-known scale available, such as degree Celsius (° C.), degree Fahrenheit (° F.), or Kelvin (K). In some cases, alternatively, the "local temperature information" may be provided in the form of a temperature range. Furthermore, it is to be noted that the "local temperature information" may be received from one or more of any of the temperature source options of step ii) which are available at a current location of the mobile device. Thus, the "local temperature information" may be a temperature value, received from a single one of the temperature source options, or it may be a temperature value, received from two or more of the temperature source options. In the latter case, the "local temperature information" may be a temperature value derived from a combination (such as an average temperature value) or from a weighted combination of two or more temperature values received by the mobile device. The term "local" used in this context refers to the temperature at the current location of the mobile device, for example, an indoor location or an outdoor location. Further, the term "local" used herein may refer to any place or area which may be specified or defined in order to appropriately represent or approximate the temperature condition at or within a locally restricted surrounding of the mobile device. For example, it usually may be appropriate to refer to a temperature condition of a region (e.g., a city, a part of a city, a neighborhood, a landscape or a part thereof, a county or a federal state, etc.), particularly if the current location of the mobile device is outdoors. In this regard, the "local temperature information" may relate to information on temperature as provided by any commonly available online weather service, as far as information on local temperatures is provided. If the current location of the mobile device is indoors, alternatively or additionally, it may be appropriate to refer to a temperature condition within a housing or within a room.

Similarly, the term "current location of the mobile device" as used herein is a broad term and is to be given its ordinary and customary meaning to a person of ordinary skill in the art and is not to be limited to a special or customized meaning. The term specifically may refer, without limitation, to any place or area which may represent or approximate a locally restricted surrounding of the mobile device. Generally, such place or area may be identified or described depending on the capabilities of the localization technique used. For example, it may be possible to locate the current location of the mobile device in a specific part of a city; a specific neighborhood or a part thereof; a specific street, address, building, or house; a specific estate, site, or parcel of land; etc.). Particularly, if the current location of the mobile device is indoors, alternatively or additionally, it may be possible to locate the current location of the mobile device within a specific housing or within a specific room.

The term "correction temperature" as used herein is a broad term and is to be given its ordinary and customary meaning to a person of ordinary skill in the art and is not to be limited to a special or customized meaning. The term specifically may refer, without limitation, to one or more of a specific temperature value, an average temperature value, a representative temperature value, a reference temperature value, a range of temperature values, and a delta temperature value, particularly a delta temperature value from a reference temperature value. The term "correction temperature function" may refer to a mathematical function, factor, formula, or algorithm, each of which may be applied by using the local temperature information received by the mobile device as an input, or as a trigger for applying said function, factor, formula, or algorithm, in the determination of the analyte concentration in step iv). Generally, the "correction temperature" and the "correction temperature function" may be useful to appropriately take into account any impact of temperature on chemical reactions as used herein in a reagent test region of an optical test strip. Such impacts may. e.g., be described by the Arrhenius equation, which is well-known to the skilled person, and which is a formula for the temperature dependence of reaction rates. In the Arrhenius equation, the variable T is the absolute temperature (in kelvins). In some cases, the determining of the analyte concentration in step iv) based on the color formation reaction at the reagent test region may be assumed to take place at typical temperatures, such as at room temperature, e.g., at about 20° C. In such cases, any temperature influence on the chemical reaction may not explicitly be represented by a factor, a formula, or an algorithm using the local temperature information received as an input; in these cases, the "correction temperature" may be determined to be set as a typical temperature, such as room temperature, e.g., at about 20° C. Alternatively, in these cases the "correction temperature function" may be determined to be a multiplication factor equal to "1," i.e., not affecting the calculation of analyte concentration.

The method may further comprise the step of displaying the analyte concentration value, such as on a display of the mobile device. Additionally or alternatively, the method may comprise storing the at least one analyte concentration value in at least one data storage device of the mobile device. Again additionally and alternatively, the method may further comprise transmitting the at least one analyte concentration value via at least one interface and/or via at least one data transmission network, such as to another computer, e.g., for further evaluation.

Accordingly, in the first aspect, this disclosure particularly relates to an analytical method for determining a concentration of an analyte, particularly blood glucose, in a body fluid, particularly blood, by using a mobile device having a camera and a processor, comprising:

i) capturing at least one image of at least a part of an optical test strip by the camera, the optical test strip having a sample of the body fluid applied onto a reagent test region of the test strip, wherein the image comprises at least a part of the reagent test region having the sample of the body fluid applied thereto; and ii) receiving local temperature information at a current location of the mobile device, wherein said local temperature information is received by the mobile device from at least two of the following temperature source options:

a) a remote weather information service;

b) a temperature sensor of an external electronic device; and c) a temperature sensor of the mobile device;

or wherein said local temperature information is received by the mobile device from a temperature sensor of an external electronic device; and wherein the external electronic device is selected from one or more of wearables, such as fitness trackers, smart watches, smart glasses, smart clothing; smart-home components, such as electronic heating systems, smart temperature measurement units, home weather stations; and body-worn sensors, such as non-invasive analyte measurement sensors; and iii) optionally, determining, by the processor, a correction temperature and/or a correction temperature function, using the local temperature information from step ii); and iv) determining, by the processor, the analyte concentration from the image captured in step i), based on a color formation reaction at the reagent test region having the sample of the body fluid applied thereto, taking into account at least one of the local temperature information from step ii), the correction temperature from step iii), and the correction temperature function from step iii).

The method proposed provides for an efficient mobile-based determination of a concentration of an analyte in a body fluid, by taking into account information on the temperature at the current location of a mobile device to be used for performing the method. The local temperature information is obtained from temperature source options which are available with low effort at said location. Thus, a reliable accuracy of the analyte measurement can efficiently be achieved, particularly with low effort for setup and implementation.

In step ii), the method may comprise determining, at least approximately, the current location of the mobile device by a localization means of the mobile device; particularly, wherein said determining is carried out automatically by the localization means. Generally, any localization means which is available to the mobile device, or is applicable to the mobile device, may be used for said determining of the current location of the mobile device. Useful localization techniques known to the skilled person comprise global navigation satellite systems (such as the Global Positioning System, GPS), localization via mobile communications network (the Global System for Mobile Communications, GSM), and WLAN-based localization (which is particularly useful for indoor localization).

Typically, said determining of the current location of the mobile device comprises using, by the localization means, data from at least one of satellites, Assisted GPS (Global Positioning System), the Global System for Mobile Communications (GSM), multilateration, triangulation, subscriber identity modules (SIM cards), software-based dedicated trackers, Wi-Fi positioning systems, Wi-Fi networks, navigation tools and navigation systems; particularly, data from satellites, and more particularly, said satellite data being selected from at least one of GPS, Galileo, and GLONASS signals. Specifically, it may be beneficial to use first satellite data from a first satellite system, and combine said first satellite data with second satellite data from a second satellite system. More specifically, the second satellite data may be used to verify the signals from the first satellite system, or to adjust the localization determined from the first satellite data, or vice versa. Thus, e.g., first satellite data may be used from Galileo, and may be combined with second satellite data from GPS. Alternatively, first satellite data may be used from GPS, and may be combined with second satellite data from Galileo.

Particularly, said determining of the current location of the mobile device may comprise selecting, by the localization means, whether the current location of the mobile device is indoors or outdoors; more particularly, wherein said selecting is carried out automatically by the localization means. Optionally, said selecting is carried out based on a number and/or on a strength of satellite signals received by the localization means. For example, the localization means may determine the current location of the mobile device to be indoors if the number of satellite signals received by the localization means is below a threshold, specifically below a pre-determined threshold, such as, e.g., 3 satellite signals received by the localization means, for at least one of a satellite system used, such as Galileo. Additionally or alternatively, the localization means may determine the current location of the mobile device to be indoors if the strength of satellite signals received by the localization means is below a pre-determined threshold. As is apparent to the skilled person, alternatively, the localization means may determine the current location of the mobile device to be outdoors if the number and/or strength of satellite signals received by the localization means is above a threshold, specifically above a pre-determined threshold.

In an embodiment, step ii) of the method may comprise checking, by the mobile device, which of the temperature source options a), b) and c) are available for receiving the local temperature information; particularly, checking at least one of:

aa) checking if a remote server is available for wirelessly connecting to the mobile device;
   bb) checking if an external electronic device is available for wirelessly connecting to the mobile device;
   cc) checking if, in the mobile device, an ambient temperature sensor and/or a temperature sensor for detecting overheating, particularly local overheating, is available.

More particularly, step ii) may comprise establishing a wireless connection of the mobile device to the remote server and/or to the external electronic device, depending on availability thereof. If a wireless connection of the mobile device to the remote server and/or to the external electronic device has been established, the local temperature information may be received from said temperature source options. Alternatively or additionally, the local temperature information may be received from an ambient temperature sensor and/or a temperature sensor for detecting overheating, if any such sensor is available in the mobile device.

Further, step ii) may comprise receiving the local temperature information from all of the temperature source options a), b) and/or c) which are available.

As indicated herein above, the external electronic device of step ii) is selected from one or more of wearables, such as fitness trackers, smart watches, smart glasses, smart clothing; smart-home components, such as electronic heating systems, smart temperature measurement units, home weather stations; and body-worn sensors, such as non-invasive or implantable analyte measurement sensors. Suitable wearables, smart-home components, and body-worn sensors are usually equipped with some means for measuring an ambient temperature, such as a temperature sensor, and with some means for wireless data transmission, such as RFID, Bluetooth or Bluetooth Low Energy (BLE), and near-field communication (NFC), and the like. Thus, an ambient temperature measured by at least one of the aforementioned devices may be transmitted wirelessly to the mobile device.

The external electronic device of step ii) may directly provide ambient temperature information, particularly for indoor locations, such that the local temperature information may be received by the mobile device, and thus may be used for determining the analyte concentration in step iv).

Similarly, in case a temperature sensor of step ii) is available in the mobile device and is an ambient temperature sensor, said ambient temperature sensor may directly provide ambient temperature information, particularly for indoor locations, such that the local temperature information may be received by the mobile device, and thus may be used for determining the analyte concentration in step iv). In case a temperature sensor of step ii) is available in the mobile device and is a temperature sensor for detecting overheating, particularly local overheating, e.g., of any component arranged inside the mobile device, said temperature sensor may provide local temperature information indirectly: For example, particularly in the case of an outdoor situation, if the temperature sensor in the mobile device indicates a very low temperature value, e.g., 10° C. or less, and the mobile device was running for a minimum amount of time, e.g., for at least 5 min, then it can be assumed that the ambient temperature in said outdoor situation is rather low, specifically lower than a moderate room temperature of 20° C., e.g., 15° C. or less. Thus, this information can be used as local temperature information at the current location of the mobile device, in combination with local temperature information from one or more of the other temperature source options.

In an embodiment of the method, step ii) comprises receiving, by the mobile device, the local temperature information from a remote weather information service; particularly, wherein the local temperature information is received from a remote server connected to the mobile device. Optionally, if the mobile device is not connected to a remote server, the local temperature information may be received from a memory of the mobile device, said memory having stored therein recent local temperature information which was previously received, by the mobile device, from the remote server. Said recent local temperature information contains local temperature information at the current location of the mobile device which can be used up to a specific point in time, calculated from the point in time when said recent local temperature information was received by the mobile device. Thus, if the time until said specific point in time has not yet elapsed, the local temperature information at the current location of the mobile device can be used from the memory of the mobile device.

In some embodiments of the method, step ii) comprises receiving, by the mobile device, the local temperature information from at least two of the temperature source options a), b) and c), such as from the temperature source options a) and b), from options a) and c), or from options b) and c); particularly from the temperature source options a) and b), or from the temperature source options a) and c); and more particularly from all of the temperature source options a), b) and c).

In other embodiments of the method, step ii) comprises receiving, by the mobile device, the local temperature information from the temperature source option b) only, i.e., from an external electronic device, which is selected from one or more of wearables, such as fitness trackers, smart watches, smart glasses, smart clothing; smart-home components, such as electronic heating systems, smart temperature measurement units, home weather stations; and body-worn sensors, such as non-invasive analyte measurement sensors.

Advantageously, step ii) comprises receiving, by the mobile device, the local temperature information from a remote weather information service, and from at least one of the temperature source options b) and c).

Optionally, the method may further comprise:

iii) determining, by the processor, a correction temperature and/or a correction temperature function, using the local temperature information from step ii).

Generally, determining a "correction temperature" and/or a "correction temperature function" may be useful to appropriately take into account any impact of temperature on chemical reactions as used herein in a reagent test region of an optical test strip. As explained further above herein, the term "correction temperature" may refer, e.g., to one or more of a specific temperature value, an average temperature value, a representative temperature value, a reference temperature value, a range of temperature values, and a delta temperature value, particularly a delta temperature value from a reference temperature value. The term "correction temperature function" may refer to a mathematical function, factor, formula, or algorithm, each of which may be applied by using the local temperature information received by the mobile device as an input or as a trigger, in the determination of the analyte concentration in step iv). Thereby, even a rather complex influence of temperature on a chemical reaction for a given reagent test chemical and a specific analyte can be taken into account for determining the analyte concentration.

For example, if the temperature itself is a variable in an equation, formula, or algorithm, each of which may be used for determining the analyte concentration by deriving said analyte concentration from the color formation reaction at the reagent test region, then the correction temperature may be a numerical temperature value which is added to or subtracted from, as appropriate, the temperature value derived from the local temperature information received by the mobile device in step ii). Alternatively or additionally, the correction temperature function may be a numerical factor (e.g., representing a %-value, such as 0.9 for 90%) which is used in the determination of the analyte concentration in step iv), e.g., by multiplication with the temperature value derived from the local temperature information, or by multiplication with the analyte concentration initially calculated (i.e., before application of the correction temperature function).

Further, if the local temperature information is assumed to be reliable, then a correction temperature value derived therefrom may be directly used as input or variable in an equation, formula, or algorithm, which may be used for determining the analyte concentration by deriving said analyte concentration from the color formation reaction at the reagent test region. The latter scenario may, e.g., apply if the local temperature information received by the mobile device is obtained from a temperature sensor of an external electronic device, such as an electronic heating system or a smart temperature measurement unit.

Furthermore, the local temperature information received by the mobile device may be subjected to one or more plausibility tests. As an example of an indoor situation, if the local temperature information is received by the mobile device from a remote weather information service, a moderate temperature, e.g., above 10° C. or above 15° C., may be assumed at the current location of the mobile device if the local temperature information received indicates an (outdoor) temperature of about typical room temperature, such as, e.g., 20° C. Furthermore, as an example of an outdoor situation, reference is made to the illustrative example given herein above with regard to a temperature sensor in the mobile device indicating a very low temperature value, e.g., 10° C. or less, and the mobile device was running for a minimum amount of time, e.g., for at least 5 min, wherein then it can be assumed that the ambient temperature in said outdoor situation is rather low, specifically lower than a typical room temperature of 20° C., e.g., 15° C. or less.

In an embodiment of the method, step iii) comprises verifying or adjusting, by the processor, the local temperature information received from at least one of the temperature source options a), b) and c), specifically from the temperature source option a). Particularly, said verifying or adjusting takes the local temperature information received from at least one of the other two temperature source options into account.

In this embodiment, said adjusting in step iii) may further comprise using a weighted average of the local temperature information received from the temperature source option a) and from at least one of the temperature source options b) and c), whereby the correction temperature or correction temperature function is determined.

In another embodiment of the method, step iii) may further comprise using the local temperature information from step ii) for selecting one of a plurality of temperature ranges, which temperature ranges may be pre-defined; particularly, selecting a temperature range which contains a local temperature derived from the local temperature information from step ii).

In this embodiment, the plurality of temperature ranges may comprise from 2 to 10, specifically from 2 to 5, such as, e.g., 2, 3, 4 or 5, temperature ranges. Specifically, using a set of at least 3, such as, e.g., 3 or 4, pre-defined temperature ranges has proven to be particularly useful for carrying out this embodiment of the method.

Furthermore, the plurality of temperature ranges may comprise at least one of a low temperature range TR(low), comprising temperatures of $T \leq T_{LOW}$, and a high temperature range TR(high), comprising temperatures of $T > T_{HIGH}$, wherein $T_{LOW}$ may be a temperature selected from the range of from 5° C. to 20° C., specifically from 10° C. to 15° C., and wherein $T_{HIGH}$ may be a temperature selected from the range of from 20° C. to 30° C., specifically from 20° C. to 25° C. If two pre-defined temperature ranges are provided, a first low temperature range TR(low) may comprise temperatures of $T \leq T_{LIMIT}$, and a second high temperature range TR(high) may comprise temperatures of $T > T_{LIMIT}$, wherein $T_{LIMIT}$ may be a temperature selected from the range of from 10° C. to 30° C., specifically of from 15° C. to 25° C., more specifically 20° C. If three pre-defined temperature ranges are provided, a first low temperature range TR(low) may comprise temperatures of $T \leq T_{LOW}$, a second medium temperature range TR(med) may comprise temperatures of $T_{LOW} < T \leq T_{HIGH}$, and a third high temperature range TR(high) may comprise temperatures of $T > T_{HIGH}$, wherein $T_{LOW}$ may be a temperature selected from the range of from 5° C. to 20° C., specifically from 10° C. to 15° C., and wherein $T_{HIGH}$ may be a temperature selected from the range of from 20° C. to 30° C., specifically from 20° C. to 25° C. Furthermore, absolute lower and/or upper limits for temperatures may be defined, such that each temperature range is clearly defined by both a lower and an upper temperature value, e.g., with TR(low) comprising temperatures of 0° C. $< T \leq T_{LOW}$, TR(med) comprising temperatures of $T_{LOW} < T \leq T_{HIGH}$, and TR(high) comprising temperatures of $T_{HIGH} < T < 40°$ C.

Each of the plurality of temperature ranges may be associated with its own correction temperature or correction temperature function, wherein said correction temperature or correction temperature function may be selected independently from one another for each temperature range. Particularly, a specific correction temperature or correction temperature function may be selected differently for each temperature range. More particularly, the specific correction temperature or correction temperature function may represent an approximate average temperature or a representative temperature of one or more of the temperature ranges. For example, in the case of three different temperature ranges, e.g., TR(low) comprising temperatures of $T \leq 15°$ C., TR(med) comprising temperatures T of 15° C. $< T \leq 25°$ C., and TR(high) comprising temperatures of $T > 25°$ C., a first correction temperature for TR(low) may be determined to be 10° C., a second correction temperature for TR(med) may be determined to be 20° C., and a third correction temperature for TR(high) may be determined to be 35° C. Each of these correction temperatures may be directly used in the determination of the analyte concentration in step iv). Alternatively, a correction temperature function may be determined for each of the temperature ranges, such as a correction factor or the like. Thus, in this example, if a local temperature information indicates a temperature value of 12° C., the first correction temperature for TR(low) will be determined to be 10° C.; and this first correction temperature of 10° C. may be taken into account in the determination of the analyte concentration in step iv). Alternatively, a first correction temperature function may be determined for the first temperature range TR(low), e.g., subtracting 10% from the analyte value initially calculated (i.e., before applying a temperature correction), corresponding to applying a multiplication factor of 0.9.

In an embodiment, the method further may advantageously comprise only allowing measurements at temperatures which are contained within a temperature range of from an absolute low temperature limit up to an absolute upper temperature limit, e.g., at temperatures of from 0° C. to 40° C. Specifically, determining whether or not a measurement is allowed may be based on at least one of the local temperature information from step ii) and the correction temperature from step iii).

Optionally, step ii) of the method may further comprise receiving additional local temperature information at a current location of the mobile device, wherein said additional local temperature information is received by the mobile device from a thermochromic field. Such a thermochromic field may be provided on the test strip and/or on a color reference card. In such a case, the image of the optical test strip captured by the camera in step i) may contain said thermochromic field, or alternatively a separate image of said thermochromic field may be captured by the camera. The additional local temperature information may be used in step iii) for determining the correction temperature, and/or in step iv) for determining the analyte concentration.

Optionally, step ii) of the method may further comprise receiving local humidity information at a current location of the mobile device, wherein said local humidity information is received by the mobile device from at least one of the following humidity source options:

a) a remote weather information service; and/or b) a humidity sensor of an external electronic device; and/or c) a humidity sensor of the mobile device.

Further, step ii) of the method may comprise determining, by the processor, a correction humidity and/or a correction humidity function, using the local humidity information; still further, step ii) of the method may comprise determining, by the processor, the analyte concentration from the image captured in step i), based on a color formation reaction at the reagent test region having the sample of the body fluid applied thereto, taking into account at least one of the local humidity information, the correction humidity, and the correction humidity function.

In another aspect of this disclosure, a mobile device having at least one camera and at least one processor is provided, the mobile device being configured for determining a concentration of an analyte in a body fluid by capturing at least one image of at least a part of an optical test strip having a reagent test region by using the camera, and by determining the at least one analyte concentration value from a color formation reaction at the reagent test region of the optical test strip, wherein the mobile device further is configured for receiving local temperature information at a current location of the mobile device, said local temperature information being received from at least two of the following temperature source options:

a) a remote weather information service;

b) a temperature sensor of an external electronic device; and c) a temperature sensor of the mobile device;

or said local temperature information being received from a temperature sensor of an external electronic device; and wherein the external electronic device is selected from one or more of wearables, such as fitness trackers, smart watches, smart glasses, smart clothing; smart-home components, such as electronic heating systems, smart temperature measurement units, home weather stations; and body-worn sensors, such as non-invasive analyte measurement sensors; and wherein the mobile device further is configured for performing at least steps iii) and iv) of the analytical method described herein above.

In another aspect of this disclosure, a kit is provided, comprising a mobile device as described herein above, and an optical test strip.

In another aspect of this disclosure, a computer program is provided, comprising instructions which, when the program is executed by the mobile device as described herein above, cause the mobile device to carry out at least steps iii) and iv) of the analytical method described herein above.

In another aspect of this disclosure, a computer-readable storage medium is provided, comprising instructions which, when executed by the mobile device as described herein above, cause the mobile device to carry out at least steps iii) and iv) of the analytical method described herein above.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 shows a flow chart of an embodiment of a method of determining a concentration of an analyte in a body fluid.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

With regard to Table 1 below, an analytical method for determining a concentration of an analyte in a body fluid by using a mobile device having a camera and a processor was used. Instead of a body fluid, a glucose reference solution of known concentration was used, and the analyte to be determined accordingly was glucose. Commercially available Accu-Chek® Active blood glucose test strips were used, which provide for blood glucose determination based on a color formation reaction at a reagent test region. Usually, such test strips are used with a corresponding Accu-Chek® Active hand-held blood glucose meter for home use by a lay user. These blood glucose meters include a temperature sensor for sensing an ambient temperature, which is used for correcting and determining the blood glucose concentration.

A "Moto G6 Plus®" mobile phone together with a software running on said mobile phone (corresponding to the software being distributed in some countries under the name AccuChek® SugarView®) was used to evaluate color formation on the reagent test region, and to determine blood glucose concentration from said color formation. The measurement procedure included a blank measurement of the dry reagent test strip without having sample applied thereto, application of a drop of blood (reference solution) to the reagent test region, waiting for a minimum amount of time for the chemical reaction taking place, and capturing an image of the reagent test region having the sample applied thereto. From the color formed on the reagent test region, the software determined a resulting blood glucose concentration. (In the AccuChek® SugarView® software, no concentration value is displayed to the user, but a corresponding blood glucose range is indicated.)

Measurements were performed at a constant relative humidity of rH=45. The glucose reference solution had a known concentration of 120 mg/dl in each case. However, the temperature was adjusted to 8° C. for a first series of measurements, to 21° C. for a second series of measurements, and to 40° C. for a third series of measurements, respectively. Each series of measurements contained 15 individual measurements.

TABLE 1

| Impact of temperature on glucose concentration, shown as deviation from the expected target glucose concentration values. "mean dev." refers to the mean deviation observed, "std" refers to the corresponding standard deviation. | | | |
| --- | --- | --- | --- |
| | n | mean dev. | std |
| Deviation glucose | | | |
| Moto G6 plus / T_Target 8 / glcT 120 / rH_Target 45 | 15 | 11.0 | 4.8 |
| Moto G6 plus / T_Target 21 / glcT 120 / rH_Target 45 | 15 | 1.7 | 2.8 |
| Moto G6 plus / T_Target 40 / glcT 120 / rH_Target 45 | 15 | −2.4 | 3.5 |
| Deviation glucose_corrected for temperature | | | |
| Moto G6 plus / T_Target 8 / glcT 120 / rH_Target 45 | 15 | −0.1 | 4.3 |
| Moto G6 plus / T_Target 21 / glcT 120 / rH_Target 45 | 15 | 1.7 | 2.8 |
| Moto G6 plus / T_Target 40 / glcT 120 / rH_Target 45 | 15 | 0.5 | 3.6 |

It has been found that, without taking a correction for a temperature deviating from about room temperature (such as about 20° C.) into account, a low temperature resulted in a positive deviation from the expected target concentration (of the glucose reference solution), whereas a high temperature led to a negative deviation from the expected target concentration. In view of the mean deviations observed in this example, a first correction temperature function, for low temperature, was set to apply a factor of 0.9 to the glucose concentrations initially calculated, resulting in a nearly complete reduction of the mean deviation. A second correction temperature function, for high temperature, was set to apply a factor of 1.03 to the glucose concentrations initially calculated, resulting in a substantial reduction of the mean deviation. At room temperature, the mean deviation was considered acceptably low. Accordingly, a third correction temperature function, for medium or room temperature, was set to apply a factor of 1.0 to the glucose concentrations initially calculated, thereby not affecting the results.

With regard to FIG. 1, which shows a flow chart of an embodiment of a method of determining a concentration of an analyte, such as blood glucose, in a body fluid, such as blood, at step 100, a mobile device having a camera and a processor is used to capture at least one image of at least a part of an optical test strip by the camera. The optical test strip has a sample of the body fluid, such as blood, applied onto a reagent test region of the test strip. The image captured comprises at least a part of the reagent test region having the sample of the body fluid applied thereto.

Also at step 100, a current location of the mobile device is determined, at least approximately, by a localization means (also referred to as a "locator") of the mobile device. Particularly, said determining may be carried out automatically by the localization means. Here, said determining of the current location of the mobile device comprises using, by the localization means, data from at least one satellite system; particularly, said satellite data may be selected from at least one of GPS, Galileo, and GLONASS signals, e.g., from Galileo satellites. Based on the number and/or the strength of the satellite signals, an indoor or an outdoor situation may be determined. Specifically, the localization means may determine the current location of the mobile device to be indoors if the number of satellite signals received by the localization means is below a pre-determined threshold, e.g., 3 satellite signals received by the localization means, for one satellite system used, such as Galileo.

If the number of signals from Galileo satellites received by the localization means is 2, then the localization means determines the current location of the mobile device to be indoors, at step 110. If the number of signals from Galileo satellites received by the localization means is more than 2, then the localization means determines the current location of the mobile device to be outdoors, at step 210. Moreover, by using the satellite signals available, the current location of the mobile device is determined or approximated as precisely as the satellite signals may allow for.

In either case, at step 300, local temperature information at the current location of the mobile device is received by the mobile device from a temperature source option available, such as from a remote weather information service, provided on a remote server and accessible via an internet connection, such as via WLAN. Such online weather information services are widely available and provide up-to-date weather information, including temperature information, essentially at every typical location identified, such as, e.g., a county, region, city, part of a city, street, neighborhood, etc. As an example, particularly for Germany, detailed information can be received from Deutscher Wetterdienst (DWD, which is the German Weather Service), but a large number of other online weather services may be used as well.

If the localization means has determined the current location of the mobile device to be indoors at step 110, the mobile device checks, at step 400, if an external electronic device having a temperature sensor is available for wirelessly connecting to the mobile device. Such external electronic device may be a smart temperature measurement unit, equipped with wireless transmission means for transmitting an ambient temperature currently measured to the mobile device. In this case, a wireless connection of the mobile device to the smart temperature measurement unit is established, such that additional local temperature information from another temperature source (the smart temperature measurement unit) is received by the mobile device, in addition to the local temperature information from the temperature source at step 300 (the remote weather information service). The local temperature information from the two temperature sources, i.e., from the remote weather information service and from the smart temperature measurement unit may be combined at step 500, e.g., the local temperature information from the two temperature sources may be compared, averaged, verified, and/or adjusted in such a combination step.

For example, at step 500, an average temperature may be calculated from both temperature values. Alternatively, the local temperature information received from the remote weather information service (generally indicating an outdoor temperature) may be verified, or adjusted, by the local temperature information received from the smart temperature measurement unit (generally indicating an indoor temperature). For example, the local temperature information received from the remote weather information service may indicate a temperature of 32° C., and the local temperature information received from the smart temperature measurement unit may indicate a temperature of 27° C.; then the processor of the mobile device may verify the local temperature information received from the remote weather information service, not changing the temperature value of 32° C. If the local temperature information received from the remote weather information service indicates a temperature of 32° C., and the local temperature information received from the smart temperature measurement unit indicates a temperature of 23° C.; then the processor of the mobile device may adjust the local temperature information received from the remote weather information service, e.g., by subtracting a third of the temperature difference between the two temperature values indicated, such that in this example 3° C. are subtracted from the initial temperature value of 32° C., giving a temperature value of 29° C. As a result, a temperature value is determined, by the processor, from the local temperature information received by the mobile device.

Said temperature value can be used as a correction temperature in the determining, at step 500, of the analyte concentration from the image captured in step 100, which is based on a color formation reaction at the reagent test region having the sample of the body fluid applied thereto. Alternatively, the local temperature information, e.g., received from the remote weather information service and verified, or adjusted, by the local temperature information received from the smart temperature measurement unit, may be used to determine a correction temperature function, which is established based on a known temperature dependence of the chemical reaction between the analyte (blood glucose) and the chemical test reagent used in the optical test element. For example, it may have been observed that measurement accuracy is affected rather differently for temperatures above and for temperatures below 30° C., respectively. In such case, measurement accuracy can be substantially increased by using a different correction temperature function for temperatures above and for temperatures below 30° C., respectively. Particularly, this aspect can advantageously be employed if the local temperature information received by the mobile device is used for selecting one of a plurality of pre-defined temperature ranges, such as 3 or 4 temperature ranges, e.g., from 0 to below 15° C., from 15 to below 25° C., from 25 to below 30° C., and from 30° C. to 40° C. Herein, it may be advantageous if each of the temperature ranges is associated with its own specific correction temperature or correction temperature function.

Furthermore, if the localization means has determined the current location of the mobile device to be indoors at step 110, and the mobile device has received local temperature information from the remote weather information service, at step 300, and from the smart temperature measurement unit, at step 400, the processor of the mobile device checks if, in the mobile device, an ambient temperature sensor and/or a temperature sensor for detecting local overheating is available, step 600. If so, additional local temperature information may be received by the mobile device from these temperature sources. In case of an ambient temperature sensor being part of the mobile device, the additional local temperature information received therefrom may be used analogously as local temperature information received, e.g., from a smart temperature measurement unit, and may be used in the determination of the analyte concentration at step 500. If a temperature sensor for detecting local overheating is included in the mobile device, one or more plausibility tests may be performed using the additional local temperature information received therefrom, at step 700.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. An analytical method for determining a concentration of an analyte in a body fluid using a mobile device having a camera and a processor, the method comprising:

i) capturing an image of at least a part of an optical test strip with the camera, the optical test strip having a sample of the body fluid applied onto a reagent test region of the test strip, wherein the image comprises at least a part of the reagent test region having the sample of the body fluid applied thereto; and ii) receiving local temperature information at a current location of the mobile device, wherein said local temperature information is received by the mobile device from at least two different temperature sources selected from the following:

a) a remote weather information service;

b) a temperature sensor of an external electronic device; and c) a temperature sensor of the mobile device;

wherein the external electronic device is selected from the group consisting of one or more of wearables and body-worn sensors; and iii) determining, by the processor, a correction temperature and/or a correction temperature function, using the local temperature information from the at least two different ones of the temperature sources of step ii); and iv) determining, by the processor, the analyte concentration from the image captured in step i), based on a color formation reaction at the reagent test region having the sample of the body fluid applied thereto, taking into account at least one of the correction temperature from step iii), and the correction temperature function from step iii).

2. The method according to claim 1, wherein step ii) comprises determining, at least approximately, the current location of the mobile device by a locator of the mobile device and wherein said determining is carried out automatically by the locator.

3. The method according to claim 2, wherein said determining of the current location of the mobile device comprises using, by the locator, data from at least one of satellites, Assisted GPS, the Global System for Mobile Communications (GSM), multilateration, triangulation, subscriber identity modules (SIM cards), software-based dedicated trackers, Wi-Fi positioning systems, Wi-Fi networks, navigation tools and navigation systems.

4. The method according to claim 2, wherein said determining of the current location of the mobile device comprises selecting, by the locator, whether the current location of the mobile device is indoors or outdoors, and wherein said selecting is carried out automatically by the locator.

5. The method according to claim 1, wherein step ii) comprises checking, by the mobile device, which of the temperature source options a), b) and c) are available for receiving the local temperature information, and checking at least one of:

aa) whether a remote server is available for wirelessly connecting to the mobile device;

bb) whether an external electronic device is available for wirelessly connecting to the mobile device; and cc) whether, in the mobile device, an ambient temperature sensor and/or a temperature sensor for detecting overheating, particularly local overheating, is available, and wherein step ii) comprises establishing a wireless connection of the mobile device to the remote server and/or to the external electronic device, depending on availability thereof and wherein step ii) further comprises receiving the local temperature information from all of the temperature source options a), b) and/or c) which are available.

6. The method according to claim 1, wherein step ii) comprises receiving, by the mobile device, the local temperature information at least from a remote weather information service and also from at least one of the temperature source options b) and c).

7. The method according to claim 1, wherein step iii) comprises verifying or adjusting, by the processor, the local temperature information received from at least one of the temperature source options a), b) and c), wherein said verifying or adjusting takes the local temperature information received from at least one of the other two temperature source options into account.

8. The method according to claim 1, wherein step iii) further comprises using the local temperature information from step ii) for selecting one of a plurality of temperature ranges, wherein the temperature ranges are, optionally, predefined and optionally comprise from 2 to 5 temperature ranges.

9. The method according to claim 8, wherein each of the plurality of temperature ranges has an associated specific correction temperature or correction temperature function, wherein said specific correction temperature or correction temperature function may be selected independently from one another for each temperature range.

10. The method according to claim 1, wherein step ii) further comprises receiving local humidity information at a current location of the mobile device, and optionally, determining, by the processor, a correction humidity and/or a correction humidity function, using the local humidity information, and determining, by the processor, the analyte concentration from the image captured in step i) by taking into account at least one of the local humidity information, the correction humidity, and the correction humidity function.

11. A mobile device having at least one camera and at least one processor, the mobile device being configured for determining a concentration of an analyte in a body fluid by capturing at least one image of at least a part of an optical test strip having a reagent test region by using the camera, and by determining the at least one analyte concentration value from a color formation reaction at the reagent test region of the optical test strip, wherein the mobile device is further configured for receiving local temperature information at a current location of the mobile device, said local temperature information being received from at least two different temperature sources selected from the following:

a) a remote weather information service;

b) a temperature sensor of an external electronic device; and c) a temperature sensor of the mobile device;

wherein the external electronic device is selected from the group consisting of one or more of wearables, smart-home components, and body-worn sensors; and wherein the mobile device further is configured for performing at least steps iii) and iv) of the analytical method according to claim 1.

12. A kit, comprising:

a mobile device according to claim 11; and an optical test strip.

13. A non-transitory computer readable medium having stored thereon computer-executable instructions for performing the method of claim 1.

14. The mobile device according to claim 11, wherein additional local temperature information is received by the mobile device from a thermochromic field provided on the test strip and/or on a color reference card.

15. The method according to claim 1, wherein additional local temperature information is received by the mobile device from a thermochromic field provided on the test strip and/or on a color reference card.

\* \* \* \* \*